US008750583B2

(12) United States Patent
Zug et al.

(10) Patent No.: US 8,750,583 B2
(45) Date of Patent: Jun. 10, 2014

(54) METHOD AND SYSTEM FOR SURGICAL MODELING

(75) Inventors: James Andrew Zug, Penryn, CA (US); Micah Aaron Forstein, Topeka, KS (US); Emil Michael Saraga, Jr., Apex, NC (US)

(73) Assignee: FUJIFILM Medical Systems USA, Inc., Stamford, CT (US)

( * ) Notice: Subject to any disclaimer, the term of this patent is extended or adjusted under 35 U.S.C. 154(b) by 103 days.

(21) Appl. No.: 13/423,345

(22) Filed: Mar. 19, 2012

(65) Prior Publication Data

US 2012/0177264 A1 Jul. 12, 2012

Related U.S. Application Data

(63) Continuation of application No. 12/287,325, filed on Oct. 8, 2008, now Pat. No. 8,160,326.

(51) Int. Cl.
*G06K 9/00* (2006.01)

(52) U.S. Cl.
USPC ........... 382/128; 382/130; 382/131; 382/132; 382/154; 600/416

(58) Field of Classification Search
None
See application file for complete search history.

(56) References Cited

U.S. PATENT DOCUMENTS

| 4,436,684 | A | 3/1984 | White |
| 5,682,886 | A | 11/1997 | Delp et al. |
| 5,824,085 | A | 10/1998 | Sahay et al. |
| 6,177,034 | B1 | 1/2001 | Ferrone |
| 7,542,791 | B2 | 6/2009 | Mire et al. |
| 7,855,723 | B2 * | 12/2010 | Preiss et al. ................... 345/419 |
| 2003/0181831 | A1 | 9/2003 | Tanaka et al. |
| 2004/0015070 | A1 | 1/2004 | Liang et al. |
| 2004/0087852 | A1 | 5/2004 | Chen et al. |
| 2004/0102866 | A1 | 5/2004 | Harris et al. |
| 2004/0171924 | A1 | 9/2004 | Mire et al. |

(Continued)

FOREIGN PATENT DOCUMENTS

| EP | 1 406 203 A2 | 4/2004 |
| WO | 00/41626 A1 | 7/2000 |

(Continued)

OTHER PUBLICATIONS

Tang, Minh Nhut, "Office Action," for U.S. Appl. No. 12/287,325, filed Oct. 8, 2008, dated Aug. 30, 2011, Alexandria, Virginia.

(Continued)

*Primary Examiner* — Minh N Tang
(74) *Attorney, Agent, or Firm* — Woods Oviatt Gilman LLP

(57) ABSTRACT

A method of surgical modeling is disclosed. A set of related two-dimensional (2D) anatomical images is displayed. A plurality of anatomical landmarks is identified on the set of related 2D anatomical images. A three-dimensional (3D) representation of at least one prosthesis is scaled to match a scale of the 2D anatomical images based at least in part on a relationship between the anatomical landmarks. 3D information from the at least one prosthesis along with information based on at least one of the plurality of anatomical landmarks is utilized to create procedure-based information. A system for surgical modeling is also disclosed. The system has a prosthesis knowledge-based information system, a patient anatomical-based information system, a user interface, and a controller. The controller has an anatomical landmark identifier, a prosthesis-to-anatomical-feature relator, and a procedure modeler.

35 Claims, 9 Drawing Sheets

(56) References Cited

U.S. PATENT DOCUMENTS

| | | |
|---|---|---|
| 2005/0038338 A1 | 2/2005 | Bono et al. |
| 2005/0059873 A1 | 3/2005 | Glozman et al. |
| 2005/0069183 A1 | 3/2005 | Ashton |
| 2005/0216305 A1 | 9/2005 | Funderud |
| 2005/0256389 A1 | 11/2005 | Koga et al. |
| 2005/0259882 A1 | 11/2005 | Dewaele |
| 2006/0098010 A1 | 5/2006 | Dwyer et al. |
| 2007/0032720 A1 | 2/2007 | Koivukangas et al. |
| 2007/0066917 A1 | 3/2007 | Hodorek et al. |
| 2008/0081982 A1 | 4/2008 | Simon et al. |
| 2008/0144773 A1* | 6/2008 | Bar-Zohar et al. ......... 378/98.12 |
| 2011/0071537 A1 | 3/2011 | Koga et al. |

FOREIGN PATENT DOCUMENTS

| | | |
|---|---|---|
| WO | 2004/001569 A2 | 12/2003 |
| WO | 2005/099636 | 10/2005 |
| WO | WO2006/092600 A1 | 9/2006 |

OTHER PUBLICATIONS

Paquit, Vincent, et al, "Near-infrared imaging and structured light ranging for automatic catheter insertion." Medical Imaging 2006: Visualization . . . ,Proc.ofSPIEv.6141 61411T.

Biocomputing Competence Centre, "Hip-Op PreOperative Planning. Hip-OpRX." www.hipop.it/hipoprx.html.2007. pp. 1-2. Casalecchio di Reno (Bo), Italia.

Biocomputing Competence Centre, "Hip-Op PreOperative Planning. HipOpCT:CT Scan Protocol." www.hipop.it/CT_protocol.html. 2007. pp. 1-2. Casalecchio di Reno (Bo), Italia.

Shaw, Grant, "Digital Templating." www.orthoview.com/. 2005. pp. 1-4. Meridian Technique Ltd., Southampton Hampshire, UK.

Artikis, T., "Extended European Search Report," for application No. EP 09 012 766.3, filed Oct. 8, 2009, dated Apr. 13, 2011, Munich, Germany.

Biocomputing Competence Centre, "HipOpCT©: 3D preoperative planning of hip replacement." www.hipop.it/surgeons.html. 2008. pp. 1-5. Casalecchio di Reno (Bo), Italia.

* cited by examiner

METHOD AND SYSTEM FOR SURGICAL MODELING

CROSS-REFERENCE TO RELATED APPLICATIONS

This application is a continuation of U.S. patent application Ser. No. 12/287,325, filed Oct. 8, 2008, now U.S. Pat. No. 8,160,326, which is hereby incorporated by reference in its entirety.

TECHNICAL FIELD

The claimed invention relates to methods for surgical modeling, and more particularly to a method and system for surgical modeling using a two-dimensional interface based on three-dimensional models and information.

BACKGROUND OF THE INVENTION

As the baby boomer generation ages, the number of hip replacement surgeries is expected to increase. In 2001, about 165,000 hip joints were replaced in U.S. hospitals according to the National Center for Health Statistics, and 326,000 knees were replaced. While the majority of joint replacement patients remain in the 60-plus year category, more people are deciding to have surgery one or two decades earlier.

About 70 percent of people seeking hip replacement surgery have severe osteoarthritis, a common chronic disease that damages cartilage, the tissue that acts as a protective cushion allowing for the smooth, low-friction movement of the joint. Osteoarthritis is the leading cause of long-term knee damage and the most common reason for knee replacement. By age 65, women are five times more likely than men to have this disease.

A common goal for physicians when replacing joints is to minimize the discomfort and the recovery time, and reduce the time it takes to successfully install the joint implant while properly installing the new joint to provide the best possible range of motion for the patient using materials and techniques which will maximize the lifetime of the replacement joint. To this end, pre-surgery modeling is an important step in the joint replacement process so that the surgeon is able to properly select the best joint replacement option and estimate how it will be implanted, move, and affect the patient prior to the actual surgery.

Unfortunately, many current pre-operation techniques only focus on selecting a prosthesis which will fit static two-dimensional requirements based on acetate portrayals of a prosthesis which are then overlaid on a two-dimensional x-ray. For example, for hip replacements, current planning for acetabular implant placement and size selection is performed using acetate templates and a single anterior-posterior X-Ray of the pelvis. Acetabular templating is most commonly performed to determine the approximate size of the acetabular component, but there is little effort to accurately determine the ideal position of the implant or the effect such placement will have on the patient.

Without accurate modeling, physicians may face uncertainty in the actual operation when deciding where to remove existing bone and/or tissue as well as how much to remove. Such uncertainty raises risks with inexperienced physicians and can also keep experienced physicians from using newer and improved joint replacement options since they are more sure of the operation experience with older technology.

Therefore, there is still a need for methods and systems which more accurately enable physicians to model surgical joint replacement.

SUMMARY OF THE INVENTION

A method of surgical modeling is disclosed. A set of related two-dimensional (2D) anatomical images is displayed. A plurality of anatomical landmarks is identified on the set of related 2D anatomical images. A three-dimensional (3D) representation of at least one prosthesis is scaled to match a scale of the 2D anatomical images based at least in part on a relationship between the anatomical landmarks. 3D information from the at least one prosthesis along with information based on at least one of the plurality of anatomical landmarks is utilized to create procedure-based information.

A system for surgical modeling is also disclosed. The system has a prosthesis knowledge-based information system, a patient anatomical-based information system, a user interface, and a controller. The controller has an anatomical landmark identifier, a prosthesis-to-anatomical-feature relator, and a procedure modeler.

A set of machine executable instructions embodied on a machine readable medium for surgical modeling is further disclosed. The set of machine executable instructions includes instructions displaying a set of related two-dimensional (2D) anatomical images. The set of machine executable instructions also includes instructions identifying a plurality of anatomical landmarks on the set of related 2D anatomical images. The set of machine executable instructions further includes instructions scaling a three-dimensional (3D) representation of at least one prosthesis to match a scale of the 2D anatomical images based at least in part on a relationship between the anatomical landmarks. The set of machine executable instructions also includes instructions utilizing 3D information from the at least one prosthesis along with information based on at least one of the plurality of anatomical landmarks to create procedure-based information.

Figure 1:
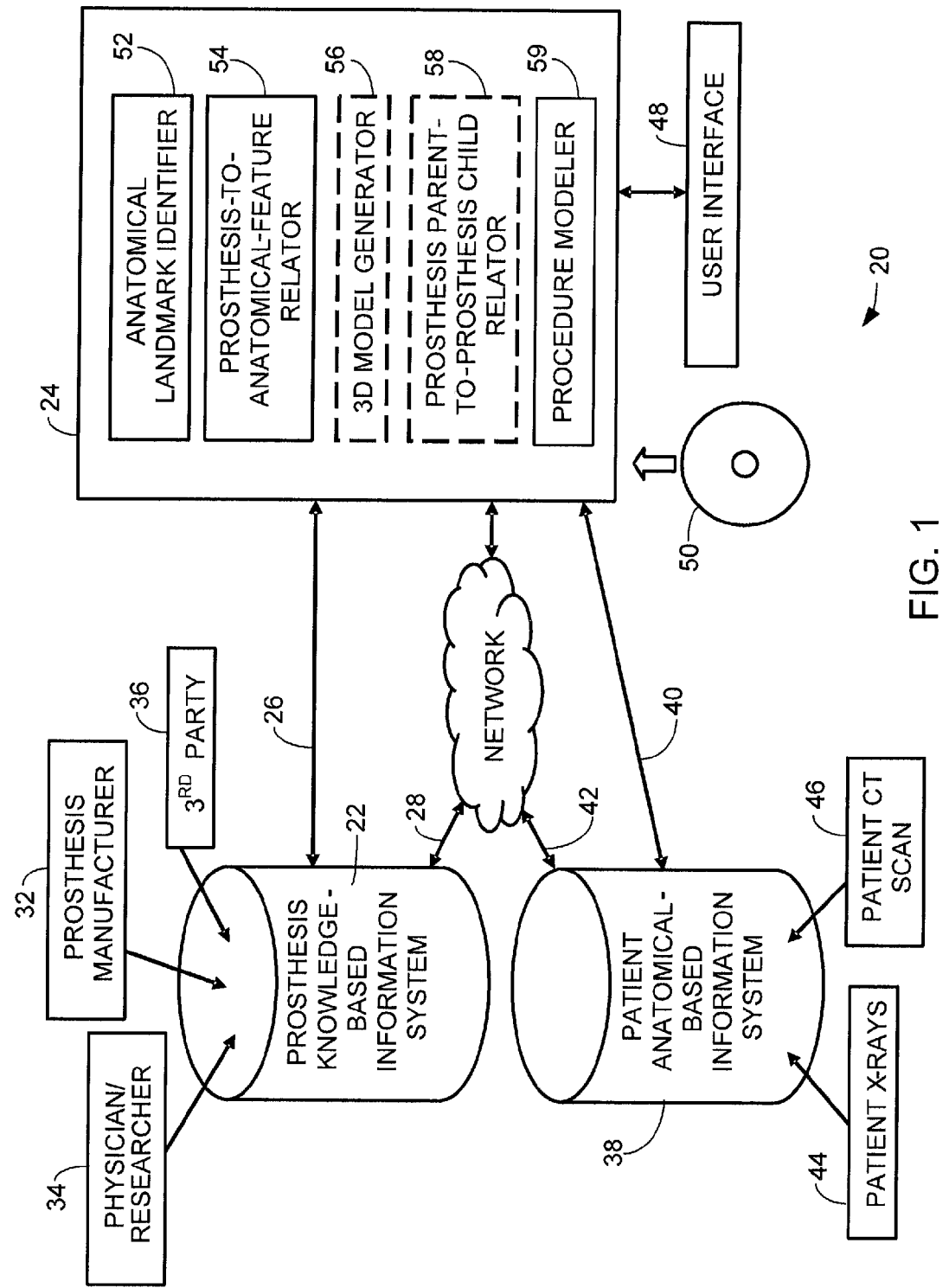
FIG. 1 schematically illustrates one embodiment of a system for surgical modeling.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION OF THE INVENTION

FIG. 1 schematically illustrates one embodiment of a system 20 for surgical modeling. The system 20 has a prosthesis knowledge-based information system 22. In some embodiments, the prosthesis knowledge-based information system 22 may be a stand-alone database or set of machine-readable files which are directly accessible 26 or remotely accessible 28, for example via a network 30, by the system's controller 24. In other embodiments, the prosthesis knowledge-based information system 22 may be a locally or internally available database or set of machine readable files. The prosthesis knowledge-based information system 22 may exist on a variety of computer readable media, including, but not limited to, randomly accessible memory (RAM), read-only memory (ROM), rewriteable flash memory, magnetic media, and optically readable/writeable media such as CD's and DVD's, or any combination thereof. The one or more computer readable media for the prosthesis knowledge-based information system 22 may be permanently installed in the system 20 or removeably installed.

The prosthesis knowledge-based information system 22 stores three-dimensional (3D) information associated with one or more prostheses. For example, the prosthesis knowledge-based information system 22 may store information defining the volume, surface area, and shape of a prosthesis. Related anatomical information for the prosthesis may also be stored, such as definitions of rotation points for the prosthesis or one or more mechanical axes for the prosthesis. The prosthesis knowledge-based information system 22 may store display information for the prosthesis, such as notes on the usage and features of the prosthesis and measurements of the prosthesis. The prosthesis knowledge-based information system 22 may also store specific locations related to the prosthesis model which can be displayed on the model. The prosthesis knowledge-based information system 22 may further store prosthesis material information. In other embodiments, the prosthesis knowledge-based information system 22 may store information which defines how one prosthesis (parent prosthesis) relates to another prosthesis (child prosthesis). Positional information for two or more related prostheses may be defined, prescribing their necessary locations relative to each other when used together and any possible degrees of freedom when moveable relative to one another.

Figure 2:
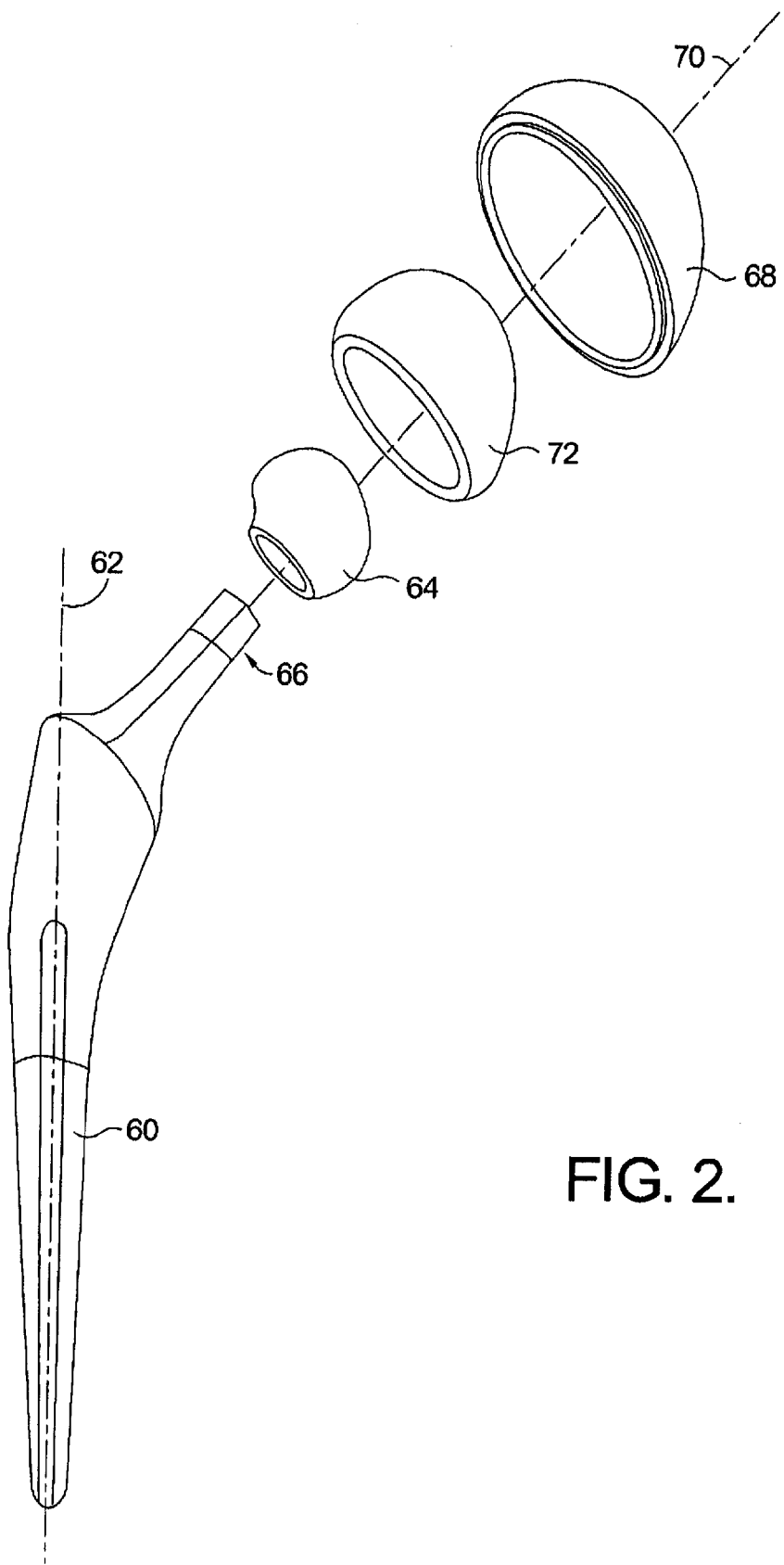
FIG. 2 schematically illustrates an embodiment of a prosthesis.

For example, FIG. 2 illustrates one embodiment of several prosthesis elements which may be used in a hip replacement. A prosthesis stem 60 may be defined as a parent prosthesis, and its surface area, volume, and shape stored in the prosthesis knowledge-based information system 22. The prosthesis stem may have a mechanical axis 62 which is definable and displayable within the system 20. In this embodiment, one of the other prosthesis elements is a prosthesis ball 64 which attaches to the neck 66 of the prosthesis stem. In this case, the ball 66 may be defined as a child prosthesis of the parent stem prosthesis 60, since the position of the ball 66 will be constrained by the position of the stem 60. A further prosthesis element in this embodiment is an acetabular cup 68 which can be installed in a pelvis socket. The acetabular cup 68 may have an associated center of rotation 70. Another prosthesis element in this embodiment is a bearing liner 72 which fits within the acetabular cup 68 to provide a bearing surface for the ball 64. The bearing liner 72 may be defined as a child prosthesis of the acetabular cup 70 or as a child of the stem 60 via the ball 64. Similarly, the acetabular cup 70 may be defined as a child of the stem 60 via the ball 64 and the bearing liner 72 or as its own parent prosthesis having a defined relationship to the stem parent prosthesis. The relationship specified in the prosthesis knowledge-based information system 22 regarding the various parent and child prostheses defines how they interrelate to each other and how they are fixed or may move relative to each other.

Returning to FIG. 1, the information stored in the prosthesis knowledge-based information system 22 may be updated or provided by a prosthesis manufacturer 32 or by a physician, clinician, or researcher 34. In other embodiments, the information stored in the prosthesis knowledge-based information system 22 may be provided by a 3rd party 36, such as a service provider which is able to model existing prostheses for manufacturers or physicians who do not have that capability.

The system 20 for surgical modeling also has a patient anatomical-based information system 38. In some embodiments, the patient anatomical-based information system 38 may be a stand-alone database or set of machine-readable files which are directly accessible 40 or remotely accessible 42, for example via a network 30, by the system's controller 24. In other embodiments, the patient anatomical-based information system 38 may be a locally or internally available database or set of machine readable files. The patient anatomical-based information system 38 may exist on a variety of computer readable media, including, but not limited to, randomly accessible memory (RAM), read-only memory (ROM), re-writeable flash memory, magnetic media, and optically readable/writeable media such as CD's and DVD's, or any combination thereof. The one or more computer readable media for the patient anatomical-based information system 38 may be permanently installed in the system 20 or removeably installed.

The patient anatomical-based information system 38 stores information associated with the anatomy of one or more patients. This may include patient images such as x-rays 44 or a CT scan 46. The anatomical information stored in the patient anatomical-based information system 38 may also include anatomical landmarks and/or anatomical mechanical axes associated with one or more of the patient images. The patient anatomical-based information system 38 may also store notes on the patient as provided by a physician or other medical practitioner for example via a user interface 48 and/or the controller 24. The patient anatomical-based information system 38 may further store a link for each patient to one or more prostheses which have been selected for possible implantation in the patient from the prosthesis knowledge-based information system 22. Furthermore, the patient anatomical-based information system 38 may store information based on the patient's images 44, 46 and the associated one or more prostheses which is generated by the controller 24 during operation of the system 20. The specific types of information related to surgical modeling which the system 20 may develop will be discussed in more detail below as such functionality is discussed.

The system also has a processor 24 which is capable of executing machine readable instructions, for example from a machine readable medium 50. Non-limiting examples of a machine readable medium 50 include a diskette, a hard drive, an optical drive, a magnetic drive, a CD, a DVD, a flash memory, a RAM, a ROM, or any combination thereof. The machine readable medium 50 may be removable from the controller, remotely available to the controller 24, permanently installed in the controller 24, or integrated with the controller 24. The controller 24 may be a microprocessor, computer, application specific integrated circuit (ASIC), analog circuitry, digital circuitry, or any combination or plurality thereof. The controller 24 may be a single unit or may be a distributed device.

Figure 3:
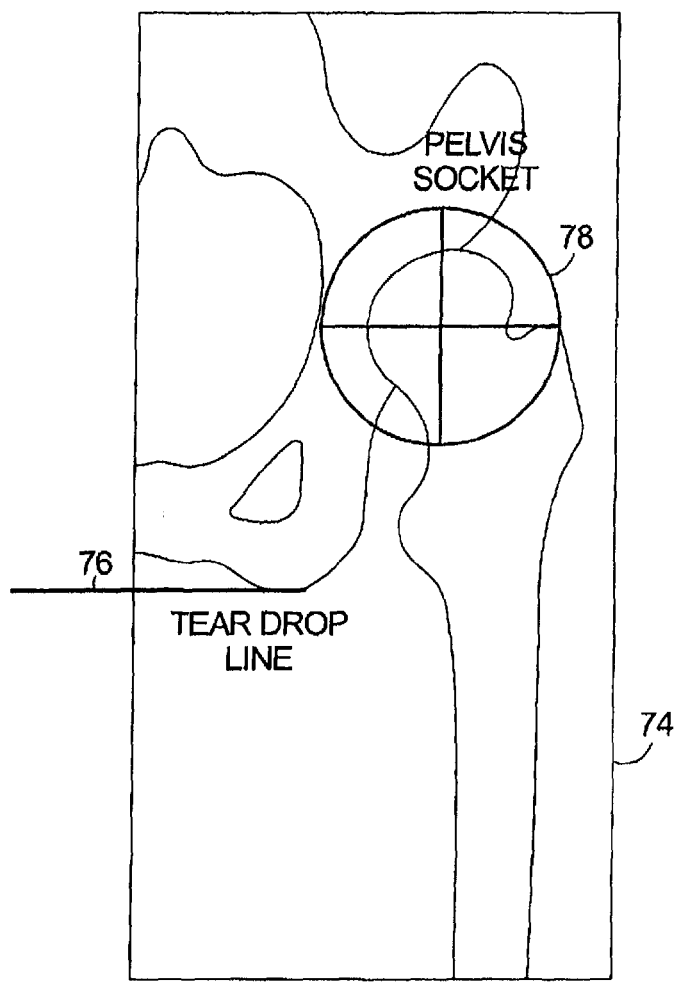
FIG. 3 schematically illustrates an embodiment of anatomical landmarks identified on a two-dimensional image.

The system 20 displays a set of related two-dimensional (2D) anatomical images on the user interface 48. The set of related 2D images may, for example, be patient x-rays or images from a patient CT scan. More than one of the set of related 2D anatomical images may be displayed on the user interface at a time, or a single image may be displayed at a time. The controller 24 has an anatomical landmark identifier 52. The actual anatomical landmarks which may be of interest can vary depending on the particular prosthesis being considered and the associated anatomy that the prosthesis would be replacing. In the case of a hip replacement, for example, the anatomical landmarks of interest may include a pelvis socket, a tear drop line, a greater trochanter, a lesser trochanter, a femoral head, a femoral ridge, and an anatomical mechanical axis. In some embodiments, the anatomical landmark identifier 52 is configured to enable a user to identify one or more anatomical landmarks manually by indicating the position of the landmark in one or more images presented on the screen. In other embodiments, the anatomical landmark identifier 52 may be configured to automatically identify some anatomical landmarks. Various automatic landmark identification methods are known to those skilled in the art. In further embodiments, the anatomical landmark identifier 52 may be configured to identify anatomical landmarks using a combination of manual and automatic methods. The anatomical landmark identifier 52 may also be configured to enable the entry of measurements on the patient images for a representation of scale. FIG. 3 illustrates an example of two anatomical landmarks which have been identified on a two-dimensional anatomic image 74. The tear drop line 76 represents the true tilt/rotation of the pelvis within the image. The pelvis socket 78 is the center of rotation of the femur within the pelvis. The one or more 2D images 74 which are displayed to a user of the system may be original 2D images, such as x-rays or a 2D image slice from a 3D CT image set.

Figure 4:
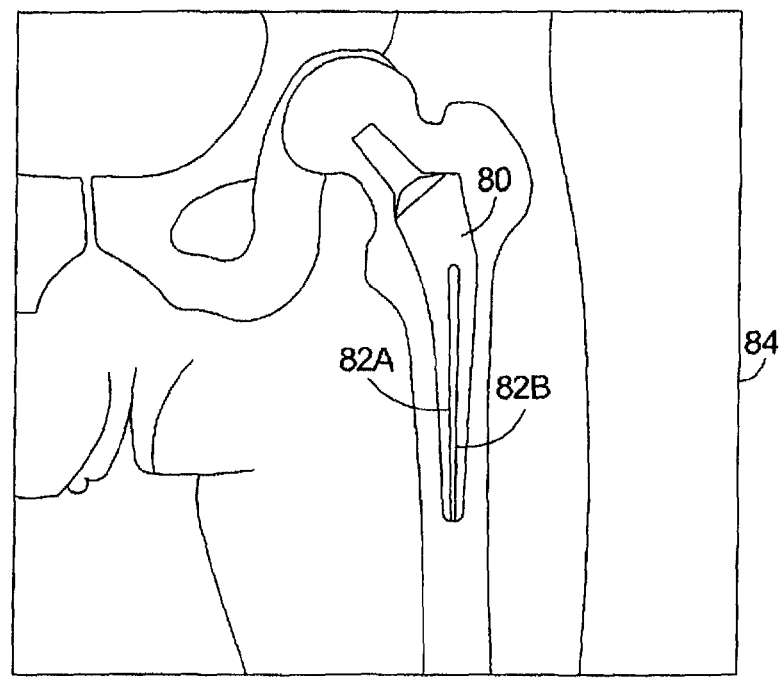
FIG. 4 illustrates an embodiment of a user interface displaying a two-dimensional representation of a three-dimensionally scaled prosthesis.

Returning to FIG. 1, the controller 24 is configured to allow a user to select one or more desired prostheses from the prosthesis knowledge-based information system 22. A 2D representation of the 3D prosthesis is displayed on the one or more patient images in the user interface 48. The controller 24 also has a prosthesis-to-anatomical-feature relator 54. The prosthesis-to-anatomical-feature relator 54 may be configured to scale the 3D prosthesis to match the scale of the anatomic image prior to creating the 2D representation. The prosthesis-to-anatomical-feature relator 54 may determine the scale of the image based on measurements from the anatomical landmark identifier 52. As an example, FIG. 4 illustrates an embodiment of a user interface displaying a two-dimensional representation of a three-dimensionally scaled prosthesis 80. The scaled prosthesis 80 may also include feature elements 82A, 82B which may schematically indicate one or more axes of rotation for the prosthesis 80. The user interface 48 may be configured to allow the scaled prosthesis 80 to be moved around within the image 84.

Figure 5:
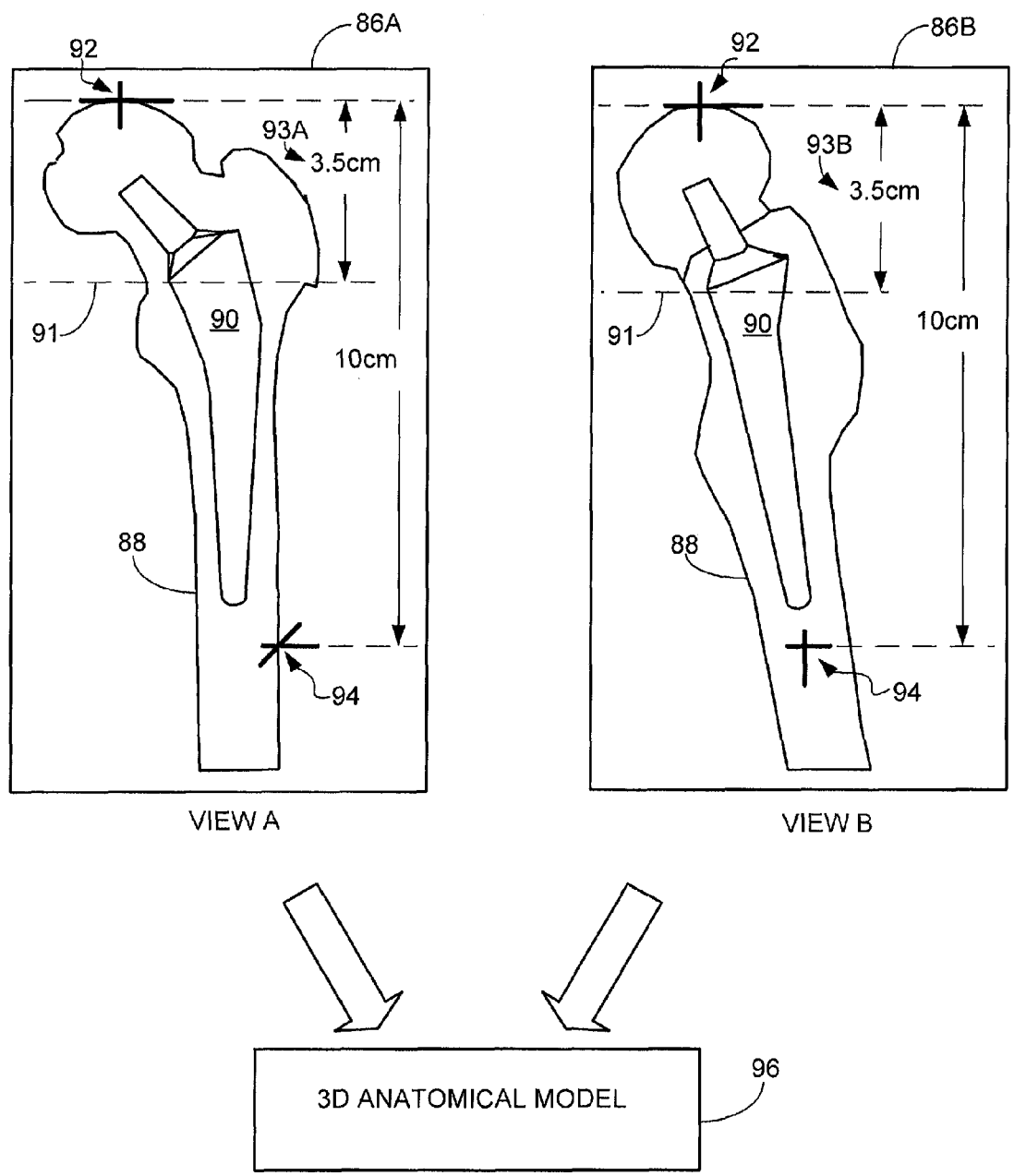
FIG. 5 schematically illustrates embodiments of two-dimensional anatomical images from different perspectives.

Returning to FIG. 1, the system may optionally have a 3D model generator 56. The 3D model generator 56 may be configured to utilize at least two images from the set of related 2D anatomical images to create a 3D anatomical model. FIG. 5 schematically illustrates two 2D anatomical images of a femur 88 having a 2D representation of a 3D prosthesis 90 overlaid on each of the views 86A, 86B. For ease of explanation, two anatomical landmarks 92, 94 have been identified on the views, and a scale between the anatomical landmarks 92, 94 determined. Based on a determination of the angular differences between the views 92, 94, a knowledge of the scale, and a knowledge of the location of one or more anatomical landmarks, the 3D model generator can develop a fit of the known points to a variety of known 3D anatomical models or modify a closest-fit 3D model so that it complies with the known constraints from the 2D images. The result is a 3D anatomical model 96 which can be used for more accurate surgical planning. Various techniques are known to those skilled in the art to produce a three-dimensional model from a set of two-dimensional images. The 3D anatomical model 96 may include the anatomical landmarks 92, 94 located in 3D. Furthermore, the prosthesis-to-anatomical-feature relator 54 may display the relationship between the anatomical landmarks located in 3D to the 3D parent prosthesis. For example, a hypothetical reference line on the prosthesis 90, such as a cut-line 91 may be automatically referenced relative to an anatomical landmark such as femur head 92. The distances relative to the cut line may be displayed, for example as in 93A, 93B, and 93C. The cut line 91 may be linked to the prosthesis per specifications from the prosthesis knowledge-based information system 22 and optionally, it may be modified by medical practitioner using the modeling system 20. The determination of a cut line for installation of a prosthesis is just one example of procedure based information which is created by the system.

Figure 6:
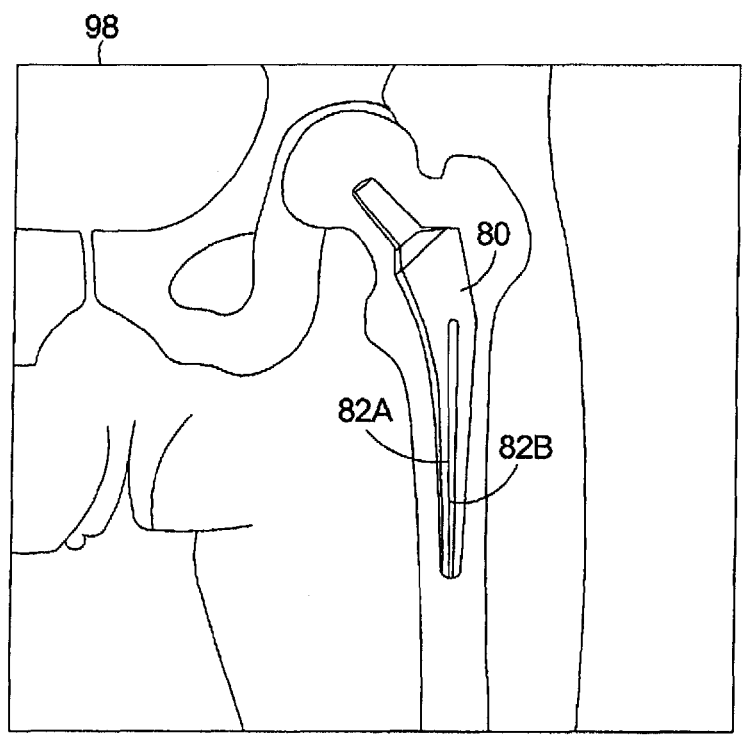
FIG. 6 illustrates an embodiment of a user interface displaying a two-dimensional representation of a rotated version of the three-dimensionally scaled prosthesis of FIG. 4.

Embodiments which develop a 3D anatomical model 96 may also be configured to enable the prosthesis-to-anatomical-feature relator 54 to determine a 3D relationship between the 3D anatomical model 96 and a 3D prosthesis model from the prosthesis knowledge-based information system 22. By determining the relationships in three-dimensions the prosthesis-to-anatomical-feature relator 54 may then develop highly accurate 2D representations of the 3D relationship which do not suffer from the limitations of the prior art which have been discussed above. Utilizing the accurate 3D relationships between the anatomical model 96 and the prosthesis, the system may be configured not only to move the prosthesis within the different images, but to rotate the prosthesis, for example, with six degrees of freedom. The rotation may also optionally be constrained to a desired axis, for example a mechanical axis of the prosthesis. FIG. 6 illustrates an embodiment of a user interface displaying a two-dimensional representation of a rotated version of the three-dimensionally scaled prosthesis of FIG. 4. The axis lines 82A, 82B from FIG. 4 have been aligned in the view of FIG. 6, while the prosthesis 80 in the 2D view 98 has been accurately adjusted based on the 3D calculations based on the relationship between the 3D anatomical model 96 and the 3D prosthesis model.

Figure 7:
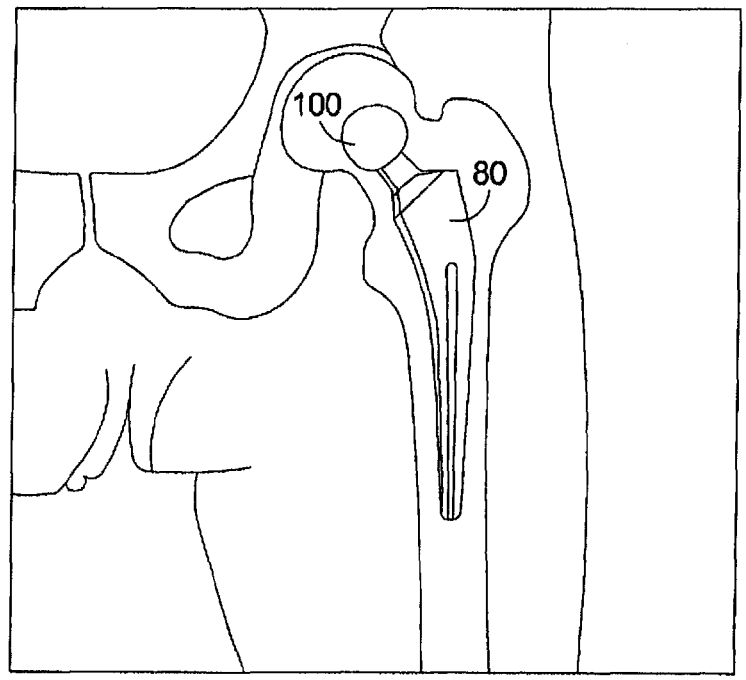
FIG. 7 illustrates an embodiment of a user interface displaying a two-dimensional representation of a three-dimensionally scaled child prosthesis in relation to the prosthesis of FIG. 5.
Figure 8:
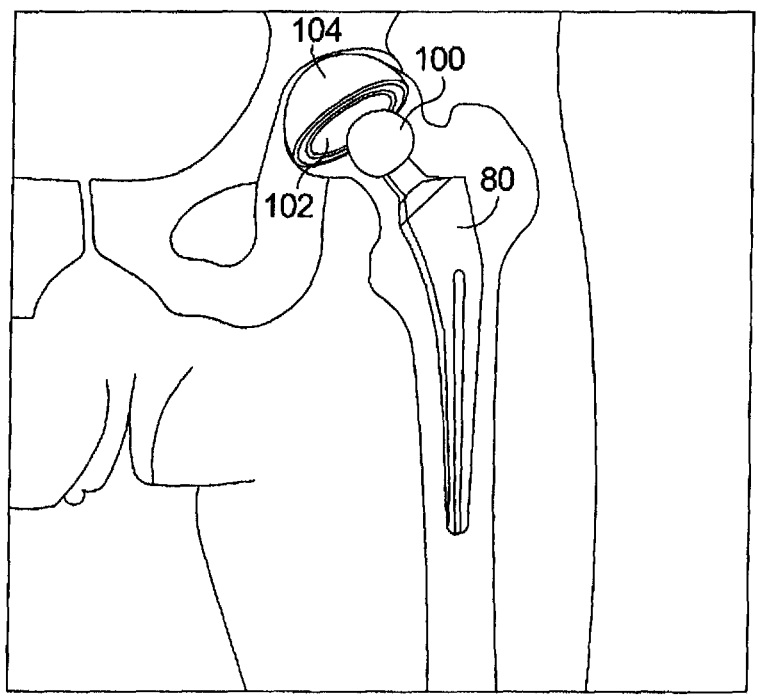
FIG. 8 illustrates an embodiment of a user interface displaying two-dimensional representations of multiple three-dimensionally scaled prostheses.

Returning to FIG. 1, the processor 24 may optionally have a prosthesis-parent-to-prosthesis-child relator 58. The prosthesis-parent-to-prosthesis-child relator 58 may be configured to determine a 3D relationship between a parent prosthesis model and a child prosthesis model from the prosthesis knowledge-based information system 22 as well as from the 3D anatomical model. As FIG. 7 illustrates, once the parent prosthesis 80 has been placed and its position is known in 3D, a child prosthesis 100 may be included in the 3D model according to its constraints. In the case of child prosthesis 100 (a ball), the child prosthesis is fixed relative to the parent prosthesis 80 (a stem). The system 20 is able to display an accurate 2D representation of this 3D relationship, and the medical practitioner operating the system 20 only has to move the parent to create a corresponding move in the child. FIG. 8 illustrates the idea that there may be multiple children prostheses 100, 102, 104 which may be associated to a parent prosthesis 80. The prosthesis knowledge-based information system 22 may define the range of motion between various prosthesis, so that, in this example the bearing liner 102 and acetabular cup 104 could be manipulated within the image only to locations compatible with the ball 100 and stem 80 location. In other embodiments, certain prostheses may be defined in the prosthesis knowledge-based information system 22 as both a parent and as a child prosthesis. For example, the acetabular cup 104 of FIG. 8 could be configured as a parent prosthesis which is moved into position relative to the 3D anatomical model independently of other prostheses. The bearing liner 102 could be a child prosthesis of the acetabular cup 104. Independent from that, the stem 80 could be a separate parent prosthesis which defines where ball 100 will end up. At some point, however, it may be useful to understand the relationship between the ball/stem combination 80,100 and the cup/liner combination 102,104. In this case, the cup 104 and liner 102 may be made child prostheses of the stem prosthesis for the purpose of determining whether the chosen placement is within a desired specification. If the placement of the prosthesis does not fall within the allowed relationship specified by the prosthesis knowledge-based information system 22, then a warning could be displayed to the user or a corrective shift could be forced on the prosthesis.

Returning to FIG. 1, the system also has a procedure modeler 59. The procedure modeler 59 utilizes 3D information from the at least one prosthesis along with information based on at least one of the plurality of anatomical landmarks to create procedure-based information. In some embodiments, calculating procedure-based information may include calculating surgical information. The surgical information could include determining the amount of bone removal necessary for implantation of the prosthesis. This can include determining a bone cut line as has been demonstrated and/or determining a volume of bone which needs to be removed from the remaining bone. This could be implemented by determining the intersection of the 3D anatomical model with the 3D prosthesis. The portion of the 3D anatomical model comprising bone which occupies the space of the 3D prosthesis would be substantially equal to the amount of bone which needed to be removed in some embodiments. In other embodiments, calculating procedure-based information may include determining a prosthesis insertion path. In further embodiments, calculating procedure-based information may include determining an area of bone contact with at least one prosthesis. This can be determined in the 3D space by calculating the surface area of the prosthesis where it intersects with the bone of the 3D anatomical model. Knowing the prosthesis contact area may also enable the system 20 to determine an amount of cement which may be needed to attach the prosthesis to the bone it is in contact with. Further embodiments may specify a desired location for the cement to contact the prosthesis, and the system 20 can be configured to display the cement contact locations as well as determine whether or not the cement locations will actually be in contact with the bone. Again, this is made possible by the 3D comparisons between the 3D prosthesis model and the 3D anatomical model.

Figure 9A:
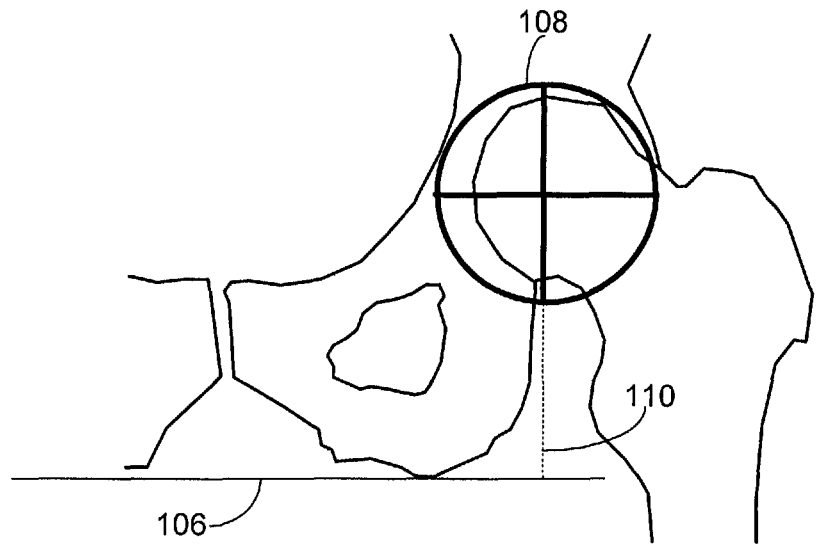
FIGS. 9A and 9B illustrates one embodiment of creating procedure-based information as part of surgical modeling.
Figure 9B:
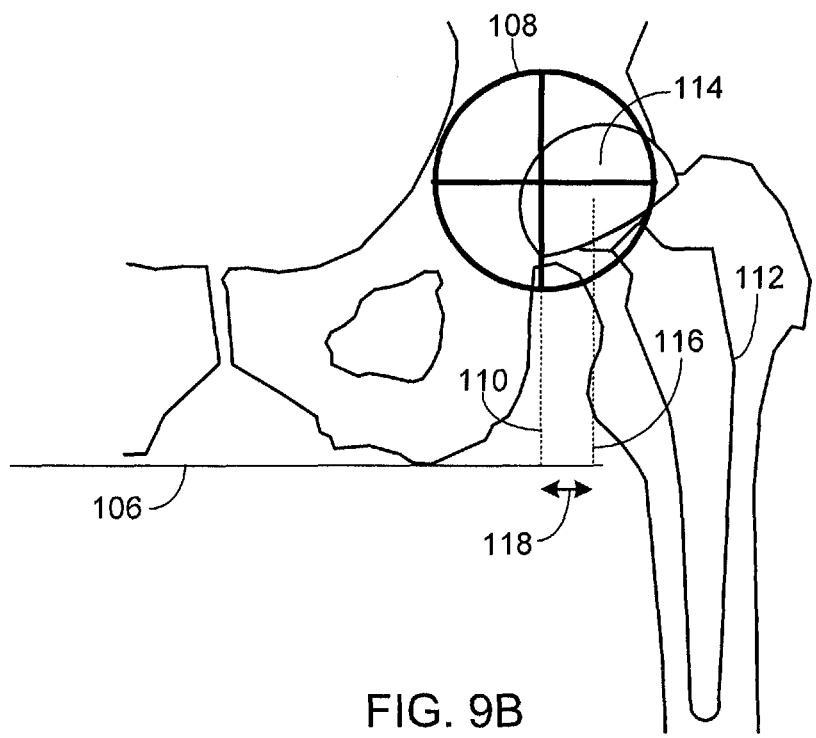

In other embodiments, the procedure-based information created by the system may be generated by comparing information from the at least one prosthesis with information from the plurality of anatomical landmarks. As an example, FIG. 9A illustrates an embodiment of a before analysis and FIG. 9B illustrates an embodiment of an after analysis with respect to a prosthesis implantation. A tear drop line 106 and a pelvis socket 108 have been identified as anatomical landmarks. The pelvis socket 108 may be projected 110 down to the tear drop line 106. Using the modeling system as previously described, a prosthesis stem 112 and its related prosthesis acetabular cup 114 may be scaled in 3D and placed within the patient image set as illustrated in FIG. 9B. The center of the acetabular cup may be projected down 116 to the tear drop line 106. The difference between where each projection 110, 116 intersects the tear drop line 106 is the lateral offset 118 or the delta change which takes place. The modeling system 20 enables such before and after comparisons by comparing the prosthesis with the anatomical landmarks.

Figure 10:
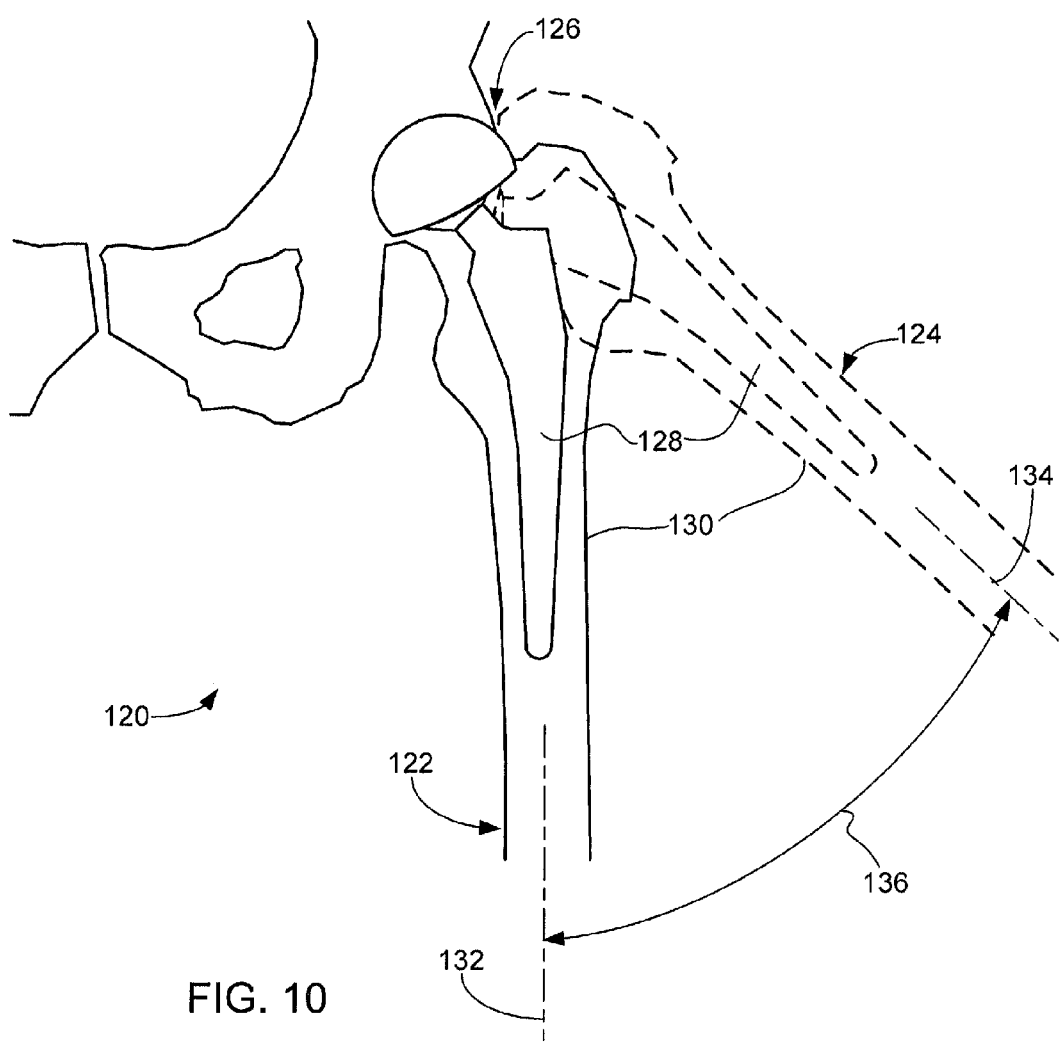
FIG. 10 illustrates another embodiment of creating procedure-based information as part of surgical modeling.

In further embodiments, the procedure-based information created by the system may include predicting a patient's range of motion based on a range of motion of the parent prosthesis and one or more child prostheses and a relationship between the parent prosthesis, the one or more child prostheses, and the 3D anatomical model. FIG. 10 schematically illustrates one embodiment of a user interface 120 which shows a baseline femur position 122 in a solid line and a laterally pivoted femur 124 in a broken line. The procedure modeler 59 may be configured to enable such manipulations to be demonstrated on-screen while using the 3D anatomical model to ensure that the different bone elements are not occupying the same space (for example, see position 126 where a top portion of the femur would contact the pelvis if it were rotated further. Additionally, the procedure modeler 59 can be configured to maintain a position of the prosthesis 128 relative to the bone 130 it is attached to. The system 20 may also be configured to compare a starting angle 132 to an ending angle 134 to determine a range 136 of motion. Further embodiments may be configured to animate this motion over a particular range.

The system 20 and its equivalents provide a medical practitioner with the ability to effectively model a surgical procedure by allowing them to test-fit various prostheses from the prosthesis knowledge-based information system 22 on a 2D or a 3D anatomical model of a subject patient while determining key procedure-based information to see if the prosthesis that fits will work and install properly. Performing the relational calculations in three-dimensions before creating the two-dimensional representations for view by the user ensure that differences in rotation, scaling, and perspective are accounted-for.

Figure 11:
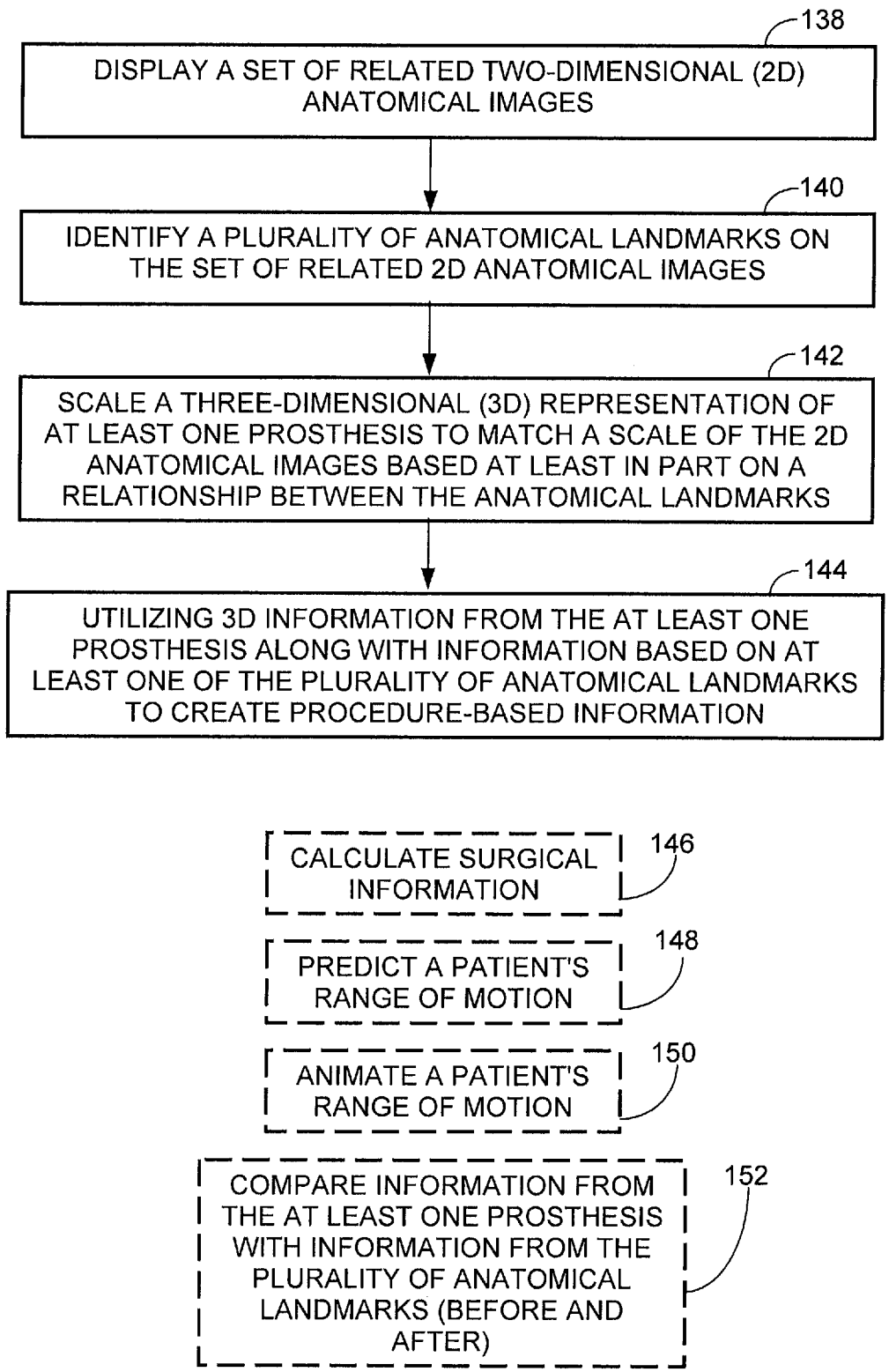
FIG. 11 illustrates one embodiment of a method for surgical modeling.

FIG. 11 illustrates one embodiment of a method for surgical modeling. A set of related two-dimensional (2D) anatomical images are displayed 138. The set of images may be displayed all at the same time, one at a time, or more than one at a time via a user interface. The 2D images may come from a variety of 2D or 3D sources, such as x-rays or a CT Scan. A plurality of anatomical landmarks are identified 140 on the set of 2D anatomical images. If the 2D anatomical images came from a 3D image set, then a 3D anatomical model may already be available.

A three dimensional (3D) representation of a parent prosthesis is scaled 142 to match a scale of the 2D anatomical images based at least in part on a relationship between the anatomical landmarks. Utilizing 3D information from the at least one prosthesis along with information based on at least one of the plurality of anatomical landmarks, procedure-based information is created 144. As discussed above, this may include calculating surgical information 146, predicting a patient's range of motion 148, animating a patient's range of motion 150, and/or comparing 152 information from the at least one prosthesis with information from the plurality of anatomical landmarks, for example to obtain a before and after picture of the prosthesis implantation.

The advantages of a system and method for surgical modeling have been discussed herein. Embodiments discussed have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A method of surgical modeling, comprising:
   displaying a set of related two-dimensional (2D) anatomical images;
   identifying a plurality of anatomical landmarks on the set of related 2D anatomical images;
   scaling a three-dimensional (3D) representation of at least one prosthesis to match a scale of the 2D anatomical images based at least in part on a relationship between the anatomical landmarks;
   utilizing 3D information from the at least one prosthesis along with information based on at least one of the plurality of anatomical landmarks to create procedure-based information; and
   determining a patient's predicted range of motion at one or more locations based on a relationship between the at least one prosthesis and a 3D anatomical model, wherein the 3D anatomical model is created from the set of related 2D anatomical images.

2. The method of claim 1, wherein creating procedure-based information comprises calculating surgical information.

3. The method of claim 2, wherein the surgical information is selected from the group consisting of an amount of bone removal, a prosthesis insertion path, an area of bone contact with the at least one prosthesis, an amount of cement, a cement contact area, and a cement location.

4. The method of claim 1, wherein creating procedure-based information comprises comparing information from the at least one prosthesis with information from the plurality of anatomical landmarks.

5. The method of claim 4, wherein comparing information from the at least one prosthesis with information from the plurality of anatomical landmarks comprises:
   determining a first intersection point between a first anatomical landmark and a second anatomical landmark projected down to the first anatomical landmark;
   determining a second intersection point between the first anatomical landmark and a prosthesis feature comparable to the second anatomical landmark projected down to the first anatomical landmark; and
   determining a delta as the difference between the first intersection point and the second intersection point.

6. The method of claim 5, wherein:
   the first anatomical landmark comprises a tear drop line;
   the second anatomical landmark comprises a pelvis socket; and
   the prosthesis feature comprises a center of an acetabular cup.

7. The method of claim 1, wherein 3D anatomical model is created using one or more of the plurality of anatomical landmarks.

8. The method of claim 1, wherein the at least one prosthesis includes a parent prosthesis and at least one child prosthesis.

9. The method of claim 8, wherein the step of determining the patient's predicted range of motion at one or more locations is further based on a range of motion of the parent prosthesis and the at least one child prosthesis.

10. The method of claim 1, further comprising displaying the patient's predicted range of motion.

11. The method of claim 1, further comprising animating the patient's predicted range of motion over a particular range.

12. A system for surgical modeling, comprising:
   a prosthesis knowledge-based information system;
   a patient anatomical-based information system;
   a user interface; and
   a controller comprising:
      a) an anatomical landmark identifier;
      b) a prosthesis-to-anatomical-feature relator;
      c) a procedure modeler; and
      d) a three dimensional (3D) model generator,
   wherein the controller is configured for displaying a set of related two-dimensional (2D) anatomical images from the patient anatomical-based information system on the user interface,
   wherein the anatomical landmark identifier is configured to identify a plurality of anatomical landmarks on the set of related 2D anatomical images using the anatomical landmark identifier,
   wherein the prosthesis to anatomical feature relator is configured to scale a three-dimensional (3D) prosthesis model of at least one prosthesis from the prosthesis knowledge-based information system to match a scale of the set of related 2D anatomical images based at least in part on a relationship between the plurality of anatomical landmarks,
   wherein the procedure modeler is configured for utilizing 3D information from the at least one prosthesis along with information based on at least one of the plurality of anatomical landmarks to create procedure-based information,
   wherein the 3D model generator is configured to utilize at least two images from the set of related 2D anatomical images to create a 3D anatomical model, wherein the 3D anatomical model comprises the plurality of anatomical landmarks located in three dimensions, and
   wherein the procedure modeler is configured for determining a patient's predicted range of motion at one or more locations based on a relationship between the at least one prosthesis and the 3D anatomical model.

13. The system of claim 12, wherein the prosthesis knowledge-based information system comprises a database having at least one data field selected from the group consisting of a 3D model of the at least one prosthesis, rotation points of the at least one prosthesis, mechanical axis of the at least one prosthesis, movement of the at least one prosthesis, orientation of the at least one prosthesis, translation of the at least one prosthesis, rotation of the at least one prosthesis, support measurements of the at least one prosthesis, material information for the at least one prosthesis, positional information for the at least one prosthesis, and degrees of freedom for the at least one prosthesis.

14. The system of claim 12, wherein the patient anatomical-based information system comprises a database having at least one data field selected from the group consisting of an X-ray, a CT scan, a patient image, an anatomical landmark, and an anatomical mechanical axis.

15. The system of claim 12, wherein the anatomical landmark identifier is configured to enable a user to identify one or more of the plurality of anatomical landmarks manually via the user interface, wherein the user interface comprises the set of related 2D anatomical images where the plurality of anatomical landmarks are identified, or
   wherein the anatomical landmark identifier is configured to enable a user to identify one or more of the plurality of anatomical landmarks automatically.

16. The system of claim 12, wherein the prosthesis to anatomical feature relator is configured to determine a 3D relationship between the 3D anatomical model and the 3D prosthesis model from the prosthesis knowledge-based information system.

17. The system of claim 12, wherein the controller further comprises a prosthesis parent to prosthesis child relator, wherein the prosthesis parent to prosthesis child relator is configured to determine a 3D relationship between the 3D prosthesis model and a 3D child prosthesis model from the prosthesis knowledge-based information system as well-as with the 3D anatomical model.

18. The system of claim 12, wherein the procedure modeler is configured to calculate surgical information.

19. The system of claim 18, wherein the surgical information is selected from the group consisting of an amount of bone removal, a prosthesis insertion path, an area of bone contact with the at least one prosthesis, an amount of cement, a cement contact area, and a cement location.

20. The system of claim 12, wherein the procedure modeler is configured to compare information from the at least one prosthesis with information from the plurality of anatomical landmarks.

21. The system of claim 12, wherein the at least one prosthesis includes a parent prosthesis and at least one child prosthesis.

22. The system of claim 21, wherein the procedure modeler is configured for determining the patient's predicted range of motion based on a range of motion of the parent prosthesis and the at least one child prosthesis, and the relationship between the at least one prosthesis and the 3D anatomical model.

23. The system of claim 12, wherein the controller is configured for displaying the patient's predicted range of motion on the user interface.

24. The system of claim 12, wherein the controller is configured for animating the patient's predicted range of motion over a particular range on the user interface.

25. A set of machine executable instructions embodied on a machine readable medium for surgical modeling, comprising:
   instructions displaying a set of related two-dimensional (2D) anatomical images;
   instructions identifying a plurality of anatomical landmarks on the set of related 2D anatomical images;
   instructions scaling a three-dimensional (3D) representation of at least one prosthesis to match a scale of the 2D anatomical images based at least in part on a relationship between the anatomical landmarks;
   instructions utilizing 3D information from the at least one prosthesis along with information based on at least one of the plurality of anatomical landmarks to create procedure-based information; and
   instructions determining a patient's predicted range of motion at one or more locations based on a relationship between the at least one prosthesis and a 3D anatomical model, wherein the 3D anatomical model is created from the set of related 2D anatomical images.

26. The set of machine executable instructions of claim 25, wherein creating procedure-based information comprises calculating surgical information.

27. The set of machine executable instructions of claim 26, wherein the surgical information is selected from the group consisting of an amount of bone removal, a prosthesis insertion path, an area of bone contact with the at least one prosthesis, an amount of cement, a cement contact area, and a cement location.

28. The set of machine executable instructions of claim 25, wherein creating procedure-based information comprises comparing information from the at least one prosthesis with information from the plurality of anatomical landmarks.

29. The set of machine executable instructions of claim 28, wherein comparing information from the at least one prosthesis with information from the plurality of anatomical landmarks comprises:
   determining a first intersection point between a first anatomical landmark and a second anatomical landmark projected down to the first anatomical landmark;
   determining a second intersection point between the first anatomical landmark and a prosthesis feature comparable to the second anatomical landmark projected down to the first anatomical landmark; and
   determining a delta as the difference between the first intersection point and the second intersection point.

30. The set of machine executable instructions of claim 29, wherein:
   the first anatomical landmark comprises tear drop line;
   the second anatomical landmark comprises a pelvis socket; and
   the prosthesis feature comprises a center of an acetabular cup.

31. The set of machine executable instructions of claim 25, wherein the 3D anatomical model is created using one or more of the plurality of anatomical landmarks.

32. The set of machine executable instructions of claim 25, wherein the at least one prosthesis includes a parent prosthesis and at least one child prosthesis.

33. The set of machine executable instructions of claim 32, wherein the step of determining the patient's predicted range of motion at one or more locations is further based on a range of motion of the parent prosthesis and the at least one child prosthesis.

34. The set of machine executable instructions of claim 25, further comprising displaying the patient's predicted range of motion.

35. The set of machine executable instructions of claim 25, further comprising animating the patient's predicted range of motion over a particular range.

* * * * *